(12) United States Patent
Hayakawa

(10) Patent No.: US 11,382,996 B2
(45) Date of Patent: Jul. 12, 2022

(54) METHOD AND APPARATUS FOR STERILIZING SLEEVE

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 326 days.

(21) Appl. No.: 16/064,648

(22) PCT Filed: Jul. 5, 2017

(86) PCT No.: PCT/JP2017/024597
§ 371 (c)(1),
(2) Date: Jun. 21, 2018

(87) PCT Pub. No.: WO2018/008670
PCT Pub. Date: Jan. 11, 2018

(65) Prior Publication Data
US 2018/0369436 A1     Dec. 27, 2018

(30) Foreign Application Priority Data
Jul. 7, 2016   (JP) .............................. JP2016-135152

(51) Int. Cl.
*A61L 2/20* (2006.01)
*B65B 55/06* (2006.01)
(Continued)

(52) U.S. Cl.
CPC ................ *A61L 2/20* (2013.01); *A61L 2/208* (2013.01); *B65B 3/025* (2013.01); *B65B 51/144* (2013.01);
(Continued)

(58) Field of Classification Search
CPC ........ A61L 2/20; A61L 2/208; A61L 2202/11; A61L 2/202; A61L 2/10; A61L 2202/15;
(Continued)

(56) References Cited

U.S. PATENT DOCUMENTS 3,120,089 A * 2/1964 Egleston ................. B29C 65/10
 53/565
4,506,491 A * 3/1985 Joosten ................... B65B 55/10
 53/426
(Continued)

FOREIGN PATENT DOCUMENTS

EP  0 232 998 A1  8/1987
EP  0 597 356 A2  5/1994
(Continued)

OTHER PUBLICATIONS

International Search Report (Application No. PCT/JP2017/024597) dated Aug. 22, 2017 (with English translation).
(Continued)

*Primary Examiner* — Regina M Yoo
(74) *Attorney, Agent, or Firm* — Burr & Brown, PLLC

(57) ABSTRACT

Provided are a method and an apparatus for sterilizing a sleeve that can shorten a sterilization process for a paper container sleeve and ensure a sterilization effect.
In a method for sterilizing a sleeve in an aseptic filling system that molds the sleeve into a paper container having a bottomed tubular shape by closing surfaces of an open end part of the sleeve and performs sterilization, filling and sealing of the paper container, the sleeve being a tubular body having walls formed by laminating at least paper, in a state where the sleeve stands in a columnar shape, heated air containing a sterilizer is blasted to an inner surface of the sleeve that is to form a bottom part of the paper container to
(Continued)

perform sterilization of the inner surface of the bottom part and heating for the closing at the same time.

7 Claims, 5 Drawing Sheets

(51) Int. Cl.
    *B65B 55/10*     (2006.01)
    *B65B 3/02*     (2006.01)
    *B65B 51/14*     (2006.01)
    *B65B 55/02*     (2006.01)
    *B65D 55/04*     (2006.01)
    *A61L 2/10*     (2006.01)
    *A61L 2/22*     (2006.01)
    *B65B 55/08*     (2006.01)
    *B65B 55/16*     (2006.01)

(52) U.S. Cl.
    CPC ............ *B65B 55/027* (2013.01); *B65B 55/06* (2013.01); *B65B 55/10* (2013.01); *B65D 55/04* (2013.01); *A61L 2/10* (2013.01); *A61L 2/202* (2013.01); *A61L 2/22* (2013.01); *A61L 2202/11* (2013.01); *A61L 2202/15* (2013.01); *A61L 2202/23* (2013.01); *B65B 55/08* (2013.01); *B65B 55/16* (2013.01)

(58) Field of Classification Search
    CPC ....... A61L 2/22; A61L 2202/23; B65B 3/025; B65B 51/144; B65B 55/027; B65B 55/06; B65B 55/10; B65B 55/08; B65B 55/16; B65D 55/04
    See application file for complete search history.

(56) References Cited

U.S. PATENT DOCUMENTS

| | | | | |
|---|---|---|---|---|
| 4,590,740 | A | * | 5/1986 | Rodocker ............... B65B 55/10 53/167 |
| 4,683,701 | A | * | 8/1987 | Rangwala ............... B65B 55/10 53/167 |
| 2002/0114727 | A1 | * | 8/2002 | McVey ................... B65B 55/10 422/4 |

FOREIGN PATENT DOCUMENTS

| | | |
|---|---|---|
| GB | 2 111 831 A | 7/1983 |
| JP | H01-52252 B2 | 11/1989 |
| JP | H09-240629 A1 | 9/1997 |
| JP | 2004-299738 A1 | 10/2004 |
| JP | 2012-136257 A1 | 7/2012 |
| JP | 2013-018535 A1 | 1/2013 |
| WO | 99/08932 A1 | 2/1999 |
| WO | 99/08934 A1 | 2/1999 |

OTHER PUBLICATIONS

Extended European Search Report and Written Opinion (Application No. 17824273.1) dated Apr. 2, 2020.

* cited by examiner

METHOD AND APPARATUS FOR STERILIZING SLEEVE

BACKGROUND OF THE INVENTION

1. Field of the Invention

The present invention relates to a method and an apparatus for sterilizing a paper container sleeve that is aseptic filled by an aseptic filling/packaging machine with milk, other milk beverages, alcohol, soup, juice, tea, water, other soft drinks, or food.

2. Description of Related Art

In conventional art, in an aseptic filling/packaging machine for a paper container, a sleeve that is to form a columnar paper container is fed, the bottom part of the container is formed, and the container is filled with a content and then sealed. For this purpose, there is proposed a method for sterilizing the paper container that involves spraying a mist of a hydrogen peroxide solution to an inner surface of the sleeve that is to form the bottom part of the paper container and drying the mist on the surface of the paper container before forming the bottom part of the container (Patent Literature 1).

It has also been proposed to sterilize the sleeve by exposing the sleeve to ethylene oxide gas or irradiating the sleeve with an electron beam before the sleeve is fed to the aseptic filling/packaging machine (Patent Literature 2). By sterilizing the sleeve in advance, the sterilization of the bottom part of the sleeve in the aseptic filling/packaging machine is omitted.

CITATION LIST

Patent Literature

Patent Literature 1: Japanese Patent Laid-Open No. H09-240629
Patent Literature 2: Japanese Patent Laid-Open No. 2013-18535

SUMMARY OF THE INVENTION

Technical Problem

According to the conventional technique of sterilizing a paper container sleeve described in Patent Literature 1, a sleeve yet to be molded into a paper container is fed to the aseptic filling/packaging machine, a mist of hydrogen peroxide solution is sprayed to a part of the sleeve that is to form the bottom part of the paper container to sterilize the part, and then heated air is blasted to the sleeve to perform removal of the mist on the surface and heating for closing the bottom part by heat sealing at the same time. However, this technique involves two steps of spraying of the mist and the blasting of the heated air, which lead to an increase in size of the aseptic filling/packaging machine and an increase in cost of the sterilization process.

The method of omitting the sterilization of the bottom part by sterilizing the sleeve in advance described in Patent Literature 2 also has a disadvantage. Specifically, if ethylene oxide gas is used for sterilization, a harmful substance can be produced in the paper which is laminated material of forming the sleeve. If a radiation such as an electron beam is used for sterilization, the radiation can cause cross-linking of polyethylene forming the innermost layer to inhibit heat sealing or decompose polyethylene to produce a strange smell. In any sterilization method, the operation is complicated, and it is also difficult to maintain the aseptic condition in the aseptic filling/packaging machine until formation of the bottom part is completed.

The present invention has been devised to solve the problems described above. An object of the present invention is to provide a method and an apparatus for sterilizing a sleeve that can simplify the process of sterilization and closing by performing sterilization of a part of a paper container sleeve that is to form a bottom part of a paper container and heating for closing the bottom part by heat sealing at the same time.

Solution to Problem

A method for sterilizing a sleeve according to the present invention is a method for sterilizing a sleeve in an aseptic filling system that molds the sleeve into a paper container having a bottomed tubular shape by closing surfaces of an open end part of the sleeve and performs sterilization, filling and sealing of the paper container, the sleeve being a tubular body having walls formed by laminating at least paper, wherein, in a state where the sleeve stands in a columnar shape, heated air containing a sterilizer is blasted to an inner surface of the sleeve that is to form a bottom part of the paper container to perform sterilization of the inner surface of the bottom part and heating for the closing at the same time.

In the method for sterilizing a sleeve according to the present invention, it is preferable that the heated air containing the sterilizer is blasted by a mandrel that has a small opening and is to be inserted into the sleeve of the columnar shape.

In the method for sterilizing a sleeve according to the present invention, it is preferable that the sterilizer contains at least hydrogen peroxide.

In the method for sterilizing a sleeve according to the present invention, it is preferable that the heated air containing the sterilizer is produced by spraying the sterilizer into an evaporating portion to gasify the sterilizer and mixing the sterilizer gas with heated air.

An apparatus for sterilizing a sleeve according to the present invention is used in an aseptic filling system that molds the sleeve into a paper container having a bottomed tubular shape by closing surfaces of an open end part of the sleeve and performs sterilization, filling and sealing of the paper container, the sleeve being a tubular body having walls formed by laminating at least paper, the apparatus including a mandrel that has a small opening and blasts heated air containing a sterilizer to an inner surface of the sleeve that is to form a bottom part of the paper container in a state where the sleeve stands in a columnar shape, the mandrel that has the small opening forming a sterilizing and closing device that performs sterilization of the inner surface of the bottom part and heating for the closing at the same time.

In the apparatus for sterilizing a sleeve according to the present invention, it is preferable that the apparatus further includes a mixing apparatus that sprays the sterilizer into an evaporating portion to gasify the sterilizer and mixing the sterilizer gas with heated air.

Advantageous Effects of Invention

According to the present invention, the process of sterilization and closing can be simplified by performing sterilization of the inner surface of the bottom part of the sleeve and heating for closing of the bottom part at the same time by blasting heated air containing the sterilizer to the inner surface of the bottom part of the sleeve that is to form the paper container.

DETAILED DESCRIPTION OF THE INVENTION

In the following, an embodiment of the present invention will be described with reference to the drawings.

(Overview of Method and Apparatus)

Figure 1:
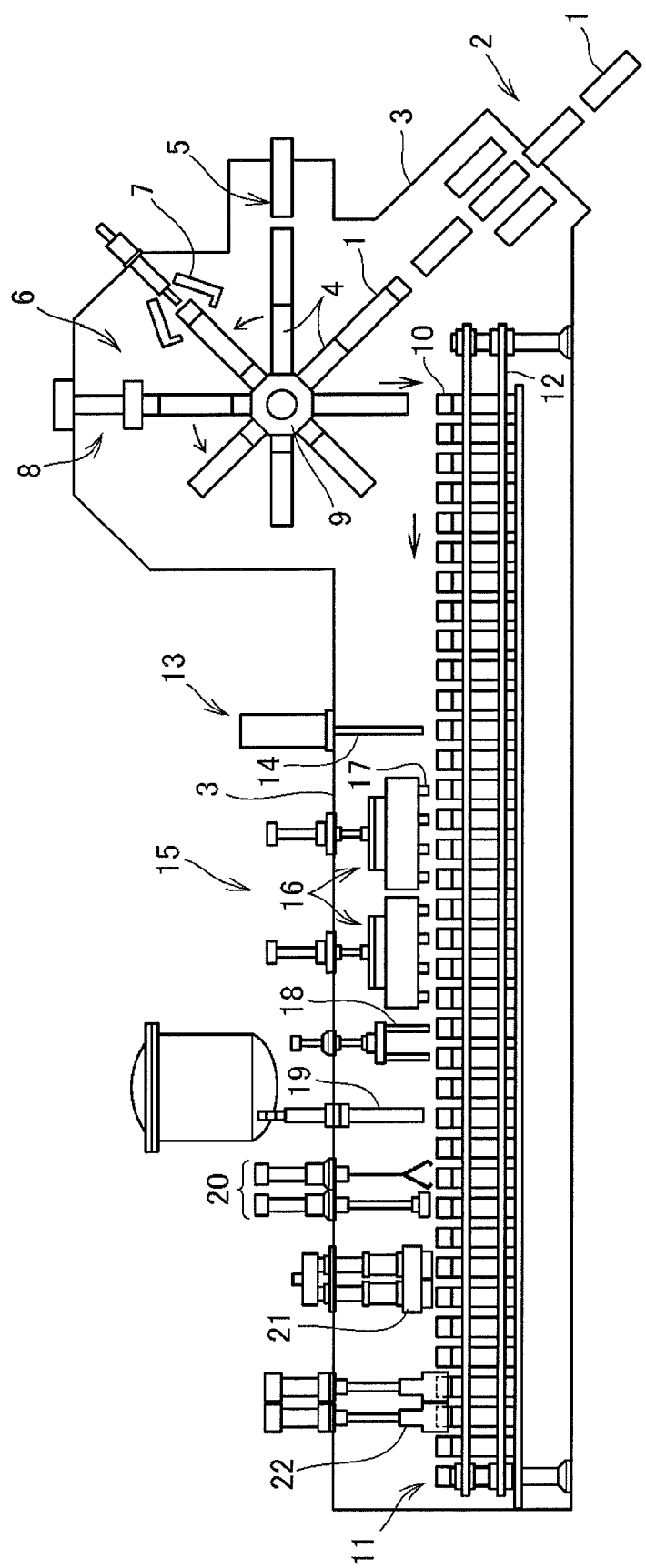
FIG. 1 is a schematic side view of an aseptic filling system incorporating an apparatus for sterilizing a sleeve according to an embodiment of the present invention.

As shown in FIG. 1, an aseptic filling system 15 that incorporates a sleeve sterilizing apparatus according to an embodiment of the present invention includes a sleeve feeding apparatus 2 that feeds a sleeve 1, a bottom part assembly apparatus 6 that receives the sleeve 1 fed from the sleeve feeding apparatus 2 and molds the sleeve 1 into a paper container 10, a conveyor 12 that conveys the molded paper container 10, an inner surface sterilizing apparatus 13 that sterilizes an inner surface of the paper container 10, a filling apparatus 19, and a top part sealing apparatus 22 that seals the paper container after filling. The aseptic filling system 15 is covered by an aseptic chamber 3.

(Overview of Process of Aseptic Filling System)

As shown in FIG. 1, the sleeve 1, which is a tubular body having walls formed by laminating at least paper, is introduced into the aseptic chamber 3 by the sleeve feeding apparatus 2. The sleeve 1 excluding a part used to close the sleeve 1 is fitted on a mandrel 4 provided on a turret 9. Furthermore, a mandrel 5 having small openings is inserted into the part of the sleeve 1 that is to form a bottom part of a paper container 10 molded from the sleeve 1 that the mandrel 4 is not inserted into, and heated air containing a sterilizer is blasted from the mandrel 5 having small openings to an inner surface of the part of the sleeve 1.

Figure 2:
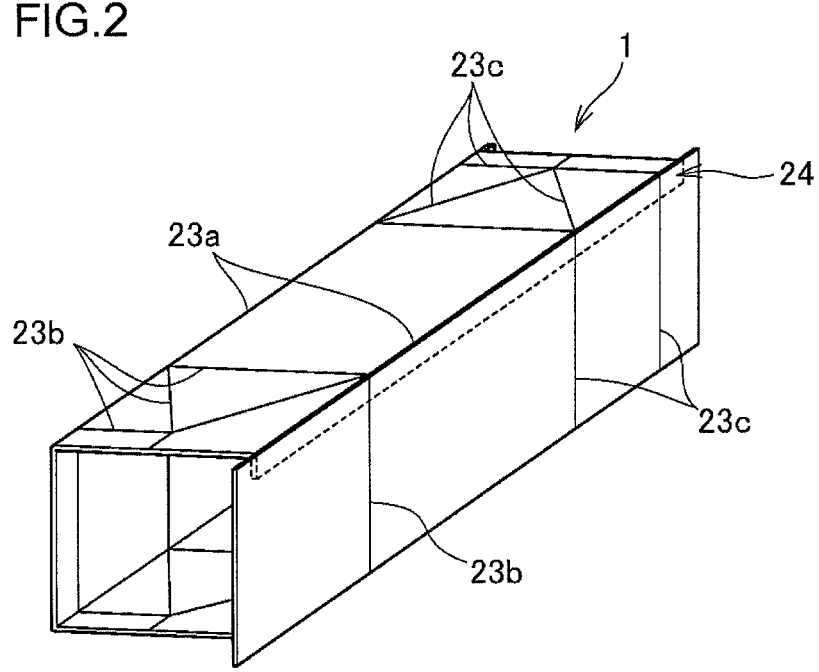
FIG. 2 shows a sleeve yet to be molded into a paper container according to the embodiment of the present invention.

As shown in FIG. 2, the sleeve 1 is formed by a sheet member formed by laminating at least paper and has an overlapping part 24 for shaping the sheet member into a tubular form, and further has a trunk part forming line 23a, a bottom part forming line 23b and a top part forming line 23c along which the sleeve 1 is folded to form the paper container. The sleeve 1 shown in FIG. 2 is molded into a gable top carton such as an aseptic filled product 11 shown in FIG. 3.

The sleeve 1 has a layer of a thermoplastic resin capable of heat sealing such as polyethylene or polypropylene on both surfaces of the paper. As required, a film of a thermoplastic resin such as polyethylene terephthalate or polyamide, an aluminum foil, a film on which a metal or metal oxide such as aluminum, silica or aluminum oxide is vapor-deposited, or a layer of a thermoplastic resin having barrier properties such as an ethylene vinyl alcohol copolymer or a copolymer of an aromatic diamine and a dibasic acid may be provided on the inside of the paper. Furthermore, a print may be on the outside or the outer most surface of the paper. As an intermediate layer, one, two or more layers of an adhesive or a thermoplastic resin having adhesion may be also provided. For example, the structure of the sleeve 1 may be polyethylene/print/paper/polyethylene, polyethylene/print/paper/polyethylene or ethylene-methacrylate copolymer/aluminum foil/polyethylene, print/polyethylene/paper/polyethylene/ethylene vinyl alcohol copolymer/polyethylene, print/polyethylene/paper/ethylene-methacrylate copolymer/polyester film having vapor-deposited silica/adhesive/polyethylene. The basis weight of the laminated paper is preferably 80 g/m$^2$ to 500 g/m$^2$. If the basis weight is lower than 80 g/m$^2$, the paper container has poor shape retention, and if the basis weight is higher than 500 g/m$^2$, the sleeve 1 is hard to process. The layer capable of heat sealing preferably has a thickness of 15 μm to 150 μm. If the thickness is smaller than 15 μm, a sufficient heat seal strength cannot be achieved, and if the thickness is greater than 150 μm, the heat seal strength is sufficient but excessive. The sleeve 1 is formed by punching such a laminate and bonding the edges of the trunk part of the punched laminate together by heat sealing.

The overlapping part 24 of the sleeve 1 is formed by heat-sealing the overlapping edges of the sleeve 1. In this process, the overlapping part 24 is formed in such a manner that the edge face of the inner laminate of the overlapping part 24 is not exposed. This is achieved by hemming, in which the tip of the end part of the inner stack is folded back to the outside, by skive hemming, in which an inner part of the tip of the end part of the inner stack is skived and the skived part is folded back to the outside, or by applying a tape that achieves heat sealing on both sides to the end part. As a result, the content can be prevented from being contaminated by a bacteria entering from the edge face of the inner paper laminate of the overlapping part 24 and from penetrating into the paper.

The sleeve 1 is folded along the trunk part forming line 23a into a tubular shape so as to provide the overlapping part 24. If the trunk part forming line 23a is shallow or the paper is thin, however, the sides of the resulting tubular sleeve 1 are arc-shaped. If the trunk part forming line 23a is partially omitted, the cross section of the part of the sleeve 1 may be substantially circular. Furthermore, the sleeve 1 can also partially have a hexagonal or other polygonal cross-sectional shape.

The sleeve 1 is further folded along the bottom part forming line 23b by a bottom part permanently folding apparatus 7, heated air containing a sterilizer is blasted to the inner surface of the sleeve 1 to melt the thermoplastic resin on the inner surface, and the folded parts forming the bottom part are bonded together under pressure by a bottom part sealing apparatus 8. As described above, the aseptic filling system according to this embodiment has an aseptically closing device that sterilizes the surface of one open end part of the sleeve 1 and closes the open end part to form a paper container 10 having a bottomed tubular shape.

Molded paper containers 10 are intermittently conveyed by the conveyor 12. A sterilizer gas is blasted from a nozzle 14 to the inner surface of the paper container 10. The sterilizer blasted to the inner surface of the paper container 10 is removed by hot air blasted from a hot air nozzle 17 to the inner surface of the paper container 10. The hot air is supplied by a hot air supplying apparatus 16. Furthermore, aseptic air may be blasted from an aseptic air nozzle 18 to the inner surface of the paper container 10.

The sterilized paper container 10 is filled with a content sterilized by a content sterilizing apparatus (not shown) by the filling apparatus 19. Furthermore, a top part permanently folding apparatus 20 folds the paper container 10 along the top part forming line 23*c*, a top part heating apparatus 21 heats the inner surface of the paper container 10, and the top part sealing apparatus 22 bonds the folded parts together under pressure to seal the top part of the paper container 10. The sealed paper container 10 is the aseptic filled product 11.

(Details of Method and Apparatus for Sterilizing Paper Container)

Figure 6:
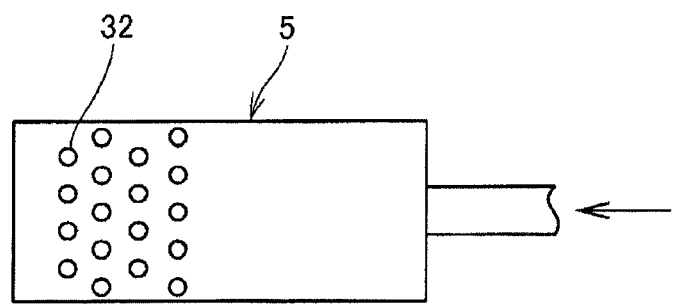
FIG. 6 shows a mandrel having small openings for blasting the heated air containing the sterilizer according to the embodiment of the present invention.
Figure 7:
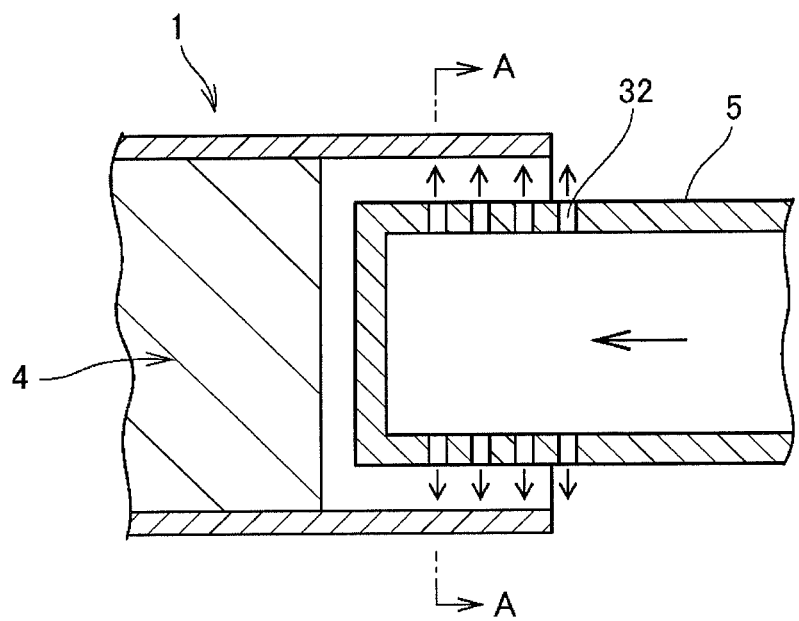
FIG. 7 is a diagram for illustrating a step of blasting the heated air containing the sterilizer to a bottom part of the sleeve according to the embodiment of the present invention.
Figure 8:
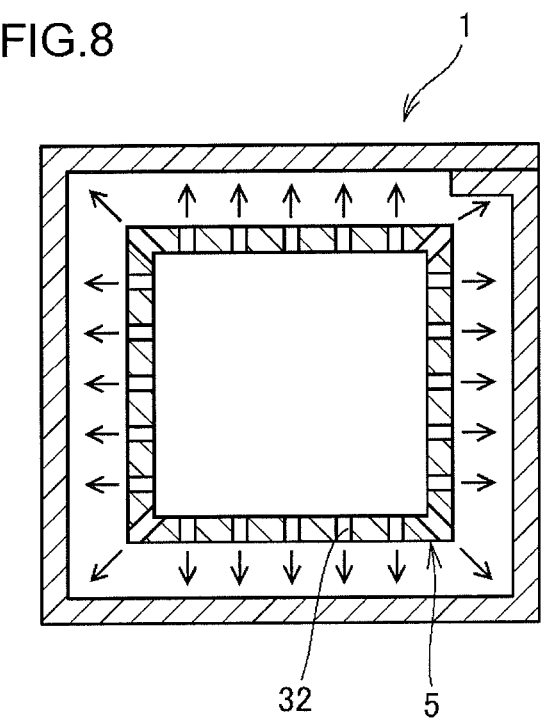
FIG. 8 is a cross-sectional view taken along the line A-A in FIG. 7, for illustrating the step of blasting the heated air containing the sterilizer to the bottom part of the sleeve according to the embodiment of the present invention.

Once the sleeve 1 is conveyed into the aseptic chamber 3, the sleeve 1 excluding the part to form the bottom part of the paper container 10 is fitted on the mandrel 4. The mandrel 5 having small openings 32 as shown in FIG. 6 is inserted into the sleeve 1, and heated air containing a sterilizer is blasted from the small openings 32 to the part of the sleeve 1 that is not in contact with the mandrel 4 as shown in FIG. 7. In this case, considering that the sleeve 1 has a rectangular cross section, the mandrel 5 having small openings has a similar rectangular cross section, and the heated air containing a sterilizer is blasted from the small openings 32 in the four surfaces of the mandrel 5 to the four inner surfaces of the sleeve 1, as shown in FIG. 8.

In this step, the inner surface of the sleeve 1 that is to form the bottom part of the paper container 10 is sterilized. After sterilization, the sterilizer is decomposed and evaporated by the heat of the heated air and does not remain on the inner surface of the sleeve 1. The blasted heated air also heats the inner surface of the sleeve 1 to a temperature at which heat sealing for closing the sleeve 1 can be achieved.

After the heated air containing a sterilizer is blasted to the sleeve 1, the bottom part permanently folding apparatus 7 folds the sleeve 1 along the bottom part forming line 23*b* in such a manner that triangular parts are folded back to the inside, and the bottom part sealing apparatus 8 bonds the folded parts together under pressure with the apexes of the triangles abutting against each other, thereby forming the paper container 10. Alternatively, the triangular parts may be folded to the outside and. In this case, after bonding, the triangular parts may be folded onto the side surface of the paper container and pasted to the outer surface of the paper container 10 or folded to the side of the heat-sealed part to form the bottom part of the paper container 10.

The sterilizer according to this embodiment preferably contains at least hydrogen peroxide. An appropriate range of the content of the hydrogen peroxide is from 0.5% by mass to 65% by mass. If the content is lower than 0.5% by mass, the sterilizing power may be insufficient. If the content is higher than 65% by mass, the sterilizer is difficult to handle from the viewpoint of safety. A more appropriate range is from 0.5% by mass to 40% by mass. When the content is equal to or lower than 40% by mass, the sterilizer is easy to handle, and the amount of the sterilizer remaining after sterilization can be reduced since the concentration is low.

Although the sterilizer contains water, the sterilizer may contain one or more of alcohols such as methyl alcohol, ethyl alcohol, isopropyl alcohol, n-propyl alcohol and butyl alcohol, ketones such as acetone, methyl ethyl ketone and acetyl acetone, and glycol ethers.

The sterilizer may further contain an additive agent such as a compound having a sterilizing effect such as peracetic acid, acetic acid, a chlorine compound or ozone; a cationic surface active agent, a non-ionic surface active agent and a phosphate compound.

Figure 4:
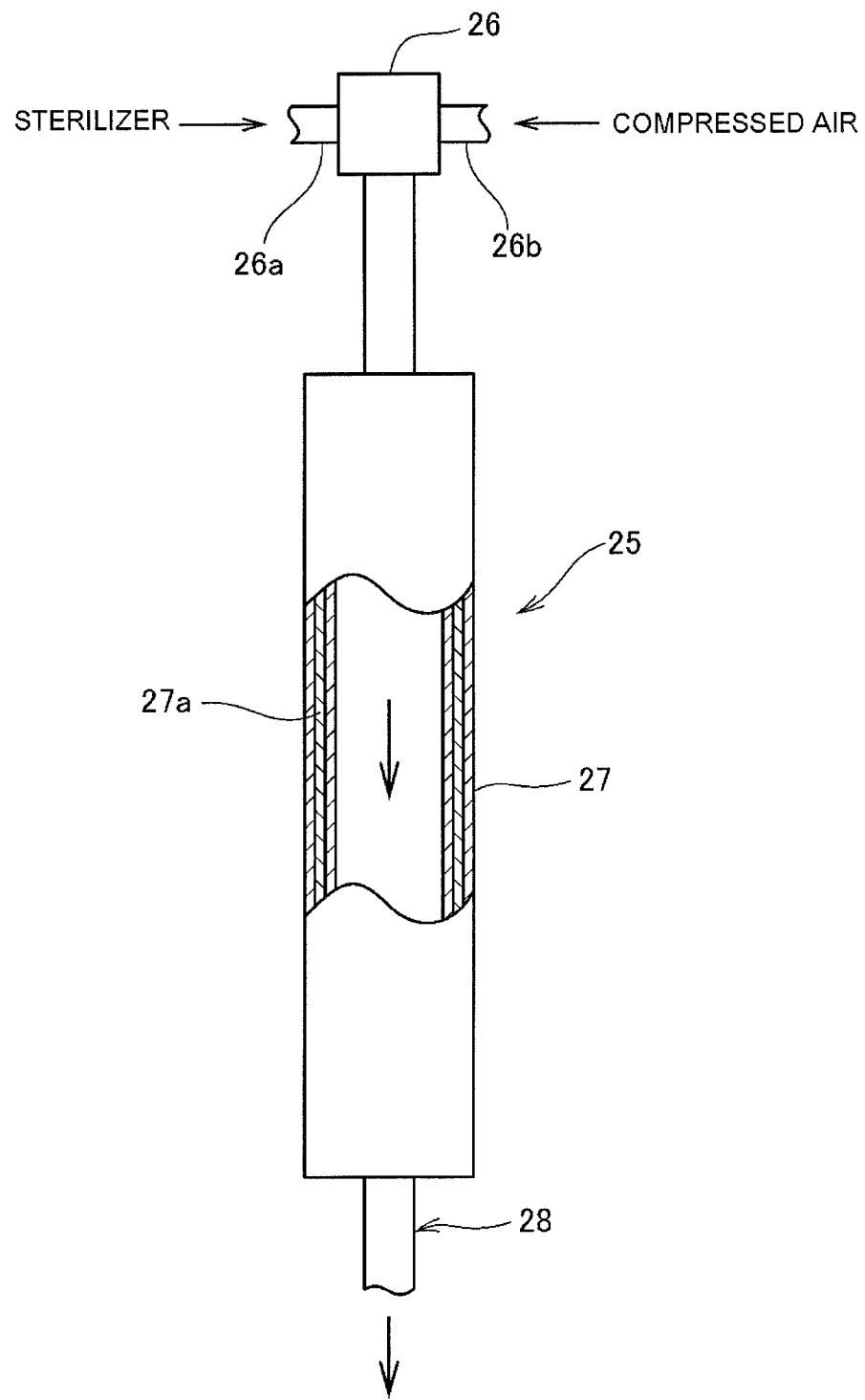
FIG. 4 shows a sterilizer gas generator incorporated in the apparatus for sterilizing a sleeve according to the embodiment of the present invention.

As shown in FIG. 4, the sterilizer is gasified by a sterilizer gas generator 25. The sterilizer gas generator 25 is provided with a sterilizer supplying portion 26 that is a twin-fluid spray nozzle for supplying the sterilizer in the form of liquid drops and an evaporating portion 27 for evaporating the sterilizer by heating the sterilizer supplied from the sterilizer supplying portion 26 to a temperature equal to or lower than the decomposition temperature of sterilizer. The sterilizer supplying portion 26 has a structure in which the sterilizer from a sterilizer supply path 26*a* and compressed air from a compressed air supply path 26*b* introduced into the sterilizer supplying portion 26 are then sprayed into the evaporating portion 27. The evaporating portion 27 is in the form of a pipe with a heater 27*a* interposed between inner and outer walls thereof, and the sterilizer blasted into the pipe is heated and evaporated. The evaporated sterilizer gas is jetted out of the evaporating portion 27 through a sterilizer jet nozzle 28. Instead of using the heater 27*a*, the evaporating portion 27 may be heated by dielectric heating.

With regard to operational conditions of the sterilizer supplying portion 26, the pressure of the compressed air is adjusted to fall within a range from 0.05 MPa to 0.6 MPa, for example. The sterilizer may be supplied by gravity or under pressure, and the supply amount can be arbitrarily set. For example, the sterilizer may be supplied at a rate of 1 g/min to 100 g/min. The inner surface of the evaporating portion 27 is heated to 140° C. to 450° C. to evaporate the sprayed sterilizer.

Figure 5:
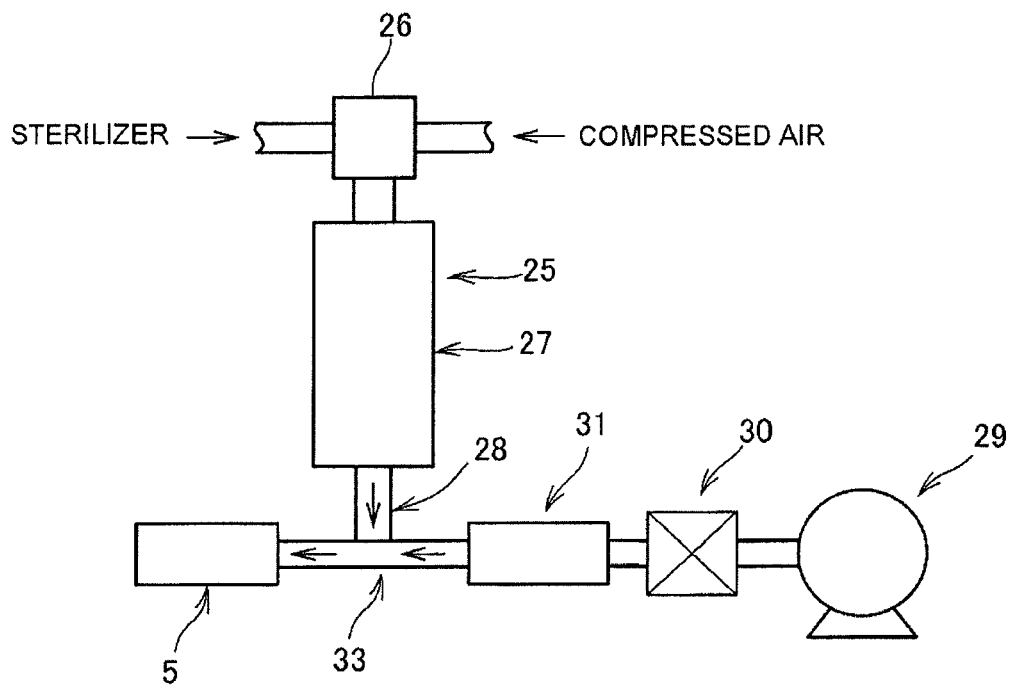
FIG. 5 shows a mixing apparatus that generates heated air containing a sterilizer according to the embodiment of the present invention.

As shown in FIG. 5, the sterilizer gas is mixed with heated air by a mixing apparatus 33. The mixing apparatus 33 mixes the sterilizer gas jetted from the sterilizer gas jet nozzle 28 with heated air obtained by sterilizing air generated by a blower 29 by passing the air through a sterilizing filter 30 and heating the air in a heating apparatus 31. The heated air mixed with the sterilizer is supplied to the mandrel 5 having small openings.

The amount of the air generated by the blower 29 varies with the volume or shape of the relevant paper container or the filling rate of the aseptic filling system 15, and can be arbitrarily set. For example, the amount of the air is set to fall within a range from 100 L/min to 1000 L/min per nozzle. The temperature of the heated air can also be arbitrarily set as far as the thermoplastic resin on the inner surface of the sleeve 1 can be molten. For example, the temperature of the heated air is typically set at 130° C. to 650° C. At a temperature lower than 130° C., the thermoplastic resin cannot be molten, and at a temperature higher than 650° C., the thermoplastic resin decomposes.

The heated air containing the sterilizer is blasted to the inner surface of the bottom part of the sleeve 1 from the small openings 32 of the mandrel 5 having small openings. The small openings 32 preferably have a circular shape and a diameter of 0.5 mm to 10 mm. The small openings 32 can have a larger size at a part that needs to be intensively heated. For example, small openings 32 for blasting heated air to triangular parts of the sleeve 1 to be heat-sealed indicated by the bottom part forming line 23b may have a larger size than the other small openings 32. This is because, when the triangular parts are folded to the inside and heat-sealed with the apexes of the triangles abutting against each other, the apexes abutting against each other need to be embedded in the thermoplastic resin on the innermost surface of the sleeve 1, and the thermoplastic resin needs to be sufficiently heated in order to achieve this. In addition, as shown in FIG. 8, when viewed in the cross section, the corners of the sleeve 1 are at greater distances from the small openings 32 than the sides of the sleeve 1. The corners of the sleeve 1 also need to be sufficiently heated. To this end, small openings 32 may be formed in the corners of the mandrel 5 having small openings, and furthermore, those small openings 32 may have a larger size than the other small openings 32. Increasing the number of the small openings 32 can have the same effect as increasing the size of the small openings 32.

After the heated air containing the sterilizer is blasted to the sleeve 1, the bottom part permanently folding apparatus 7 folds the triangular parts of the sleeve 1 to the inside along the bottom part forming line 23b. After that, the folded parts are bonded together under pressure between the bottom part sealing apparatus 8 and the mandrel 4 on which the sleeve 1 is fitted to form the bottom part. In this way, the sleeve 1 is molded into the paper container 10. In the case where the triangular parts are folded to the outside along the bottom part forming line 23b, the triangular parts are folded back onto the side surface or outer surface of the paper container 10 after the parts to be heat-sealed are bonded under pressure. In this case, to bond the triangular parts to the side surface or outer surface of the paper container 10, hot air may be blasted to the parts to be bonded, or a hot-melt adhesive may be applied to the parts to be bonded.

Whether the triangular parts are folded to the inside to abut against each other or folded to the outside, there is a part that is not exposed to the inside of the paper container 10 on the inner surface of the bottom part of the molded paper container 10. Although the sterilizer gas is blasted to the inner surface of the paper container 10 for sterilization in the next step, the part that is not exposed is difficult to sterilize. According to this embodiment, the parts of the sleeve 1 to form the bottom part of the paper container 10 are sterilized before forming the bottom part, and therefore, an aseptic filled product 11 that is highly sterilized can be advantageously obtained.

As shown in FIG. 1, the sterilizer gas is blasted from the nozzle 14 to the inner surface of the paper container 10. The nozzle 14 may blast the sterilizer gas to the inner surface of the paper container 10 from above the open end of the paper container 10. To ensure sterilization of the inner surface of the paper container 10, alternatively, the nozzle 14 may be inserted into the paper container 10 before blasting the sterilizer gas.

The sterilizer is gasified by a sterilizer gas generator, which is similar to the sterilizer gas generator 25 shown in FIG. 4. The sterilizer may be the same as the sterilizer used to sterilize the bottom part of the sleeve 1.

The sterilizer gas exiting the nozzle 14 flows to the inner surface of the paper container 10 in the form of gas, mist of the condensate thereof, of a mixture thereof.

Hot air, which is produced by sterilizing air through a sterilizing filter and heating the sterilized air, may be supplied at a middle of the nozzle 14. This increases the injection pressure of the sterilizer gas from the nozzle 14 and thus the blast pressure of the sterilizer gas. The hot air prevents condensation of the sterilizer gas to improve the efficiency of sterilization. The temperature of the hot air can be set at 50° C. to 150° C. If the temperature is lower than 50° C., the hot air promotes condensation of the sterilizer gas. If the temperature is higher than 150° C., when the innermost layer of the paper container 10 is made of polyethylene, the heat-sealed polyethylene layers may peel off.

In FIG. 1, immediately before the sterilizer gas is blasted to the paper container 10, the paper container 10 may be preliminarily heated by blasting heated air to the paper container 10. The preliminary heating can further improve the sterilization effect on the inner surface of the paper container 10.

Instead of providing only one nozzle 14, a plurality of nozzles 14 may be arranged along the traveling path of the paper container 10, and the sterilizer gas may be blasted to the paper container 10 from the nozzles 14 at a plurality of times.

Hot air may be further blasted to the paper container 10 after the sterilizer gas is blasted to the paper container 10. The blasted hot air activates the hydrogen peroxide on the surface of the paper container 10. By blasting the hot air, the sterilizer on the paper container 10 is quickly removed from the surface of the paper container 10.

The temperature of the hot air can be set at 50° C. to 150° C. A temperature lower than 50° C. is insufficient to activate the sterilizer. If the temperature is higher than 150° C., when the innermost layer of the paper container 10 is made of polyethylene, the heat-sealed polyethylene layers may peel off.

Instead of providing only one hot air nozzle 17, a plurality of hot air nozzles 17 may be arranged along the traveling path of the paper container 10, and the hot air may be blasted to the paper container 10 from the hot air nozzles 17 at a plurality of times.

Furthermore, although the hot air nozzle 17 may blast the hot air to the inner surface of the paper container 10 from above the open end of the paper container 10, to ensure removal of the sterilizer on the inner surface of the paper container 10, the hot air nozzle 17 may be inserted into the paper container 10 before blasting the hot air.

Furthermore, after the hot air is blasted to the paper container 10, aseptic air, which is produced by sterilizing air through a sterilizing filter, may be blasted to the inner surface of the paper container 10 from an aseptic air nozzle 18. The blasted aseptic air removes the sterilizer remaining in the paper container 10 or a substance giving out a strange smell that derives from polyethylene forming the innermost surface of the paper container 10 and is produced because of the hot air.

After the paper container 10 is filled with a content, the inner surfaces of the open end part of the paper container 10 are heat-sealed to close the paper container 10. In this way, the aseptic filled product 11 is obtained. In the heat sealing, after the inner surfaces are heated by hot air, triangular parts may be folded to the inside along the top part forming line 23c and bonded together under pressure with the apexes of the triangles abutting against each other. Alternatively, the triangular parts may be folded to the outside, and after bonding under pressure, the triangular parts may be folded onto the side surface of the paper container and pasted to the outer surface of the paper container 10 or folded to the side of the heat-sealed parts. In the latter case, the top part is flat, and the aseptic filled product 11 has a brick shape, rather than the gable top shape shown in FIG. 3. Alternatively, the heat sealing may be achieved by folding the triangular parts to the outside and performing external heating, ultrasonic heat sealing, or high frequency heat sealing if the sleeve 1 includes a layer of aluminum foil.

Figure 3:
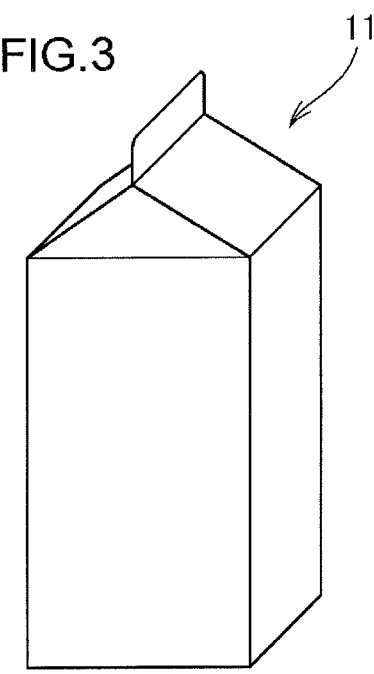
FIG. 3 shows an aseptic filled product according to the embodiment of the present invention.

A spout may be provided on the top part of the aseptic filled product 11 shown in FIG. 3.

Aseptic air is supplied into the aseptic chamber 3 to constantly keep the interior of the aseptic chamber 3 at positive pressure, so that the aseptic filling system 15 can maintain the aseptic condition achieved by the sterilization operation in the aseptic chamber 3 performed before operation of the aseptic filling system 15 and prevent the interior from being contaminated by bacteria in the outside air. The sterilization operation performed before operation of the aseptic filling system 15 may be sterilization of the interior of the aseptic chamber 3 by a mist of 1 mg/L to 300 mg/L of hydrogen peroxide, for example. Alternatively, the portions that are to come into contact with the sleeve 1 or paper container 10 may be irradiated with light containing ultraviolet rays, or a chemical containing 1% by mass of ethanol or hydrogen peroxide may be sprayed to those portions. In the aseptic filling system 15, the bottom part assembly apparatus 6, the inner surface sterilizing apparatus 13 including the nozzle 14 for blasting the sterilizer gas and the hot air nozzle 17, the filling apparatus 19, the sealing apparatuses including the top part sealing apparatus 22 may be partitioned into zones, and aseptic air may be supplied to each zone with the pressure of the supplied aseptic air being changed stepwise from the zone of the filling apparatus 19 to the outer zones.

EXAMPLES

In the following, examples of the present invention will be described.

(Method of Operation)

Sleeve 1 that had a square cross section having a side length of 75 mm and were to form a paper container 10 having a volume of 1000 ml as shown in FIG. 2 were produced. The structure of the sleeves 1 was as follows: a polyethylene layer having a thickness of 25 µm, a layer of paper having a basis weight of 300 g/m², a layer of ethylenemethacrylate copolymer having a thickness of 20 µm, a polyester film including deposited silica having a thickness of 12 µm, a layer of an adhesive, and a layer of polyethylene having a thickness of 55 µm. Using this sleeve 1, the following operations were performed.

A hydrogen peroxide solution containing 35% by mass of hydrogen peroxide was used as the sterilizer. The sterilizer gas was generated by supplying compressed air at 0.5 MPa and the hydrogen peroxide solution as the sterilizer at a rate of 10 ml/min to the sterilizer gas generator 25 shown in FIG. 4 and heating the evaporating portion 27 until the surface temperature reached 300° C. The sterilizer gas was mixed, in the mixing apparatus 33, with aseptic air produced by passing air through the sterilizing filter 30 and heating the sterilized air to 300° C. by the heating apparatus 31. The heated air mixed with the sterilizer was supplied to the mandrel 5 having small openings, the mandrel 5 having small openings was inserted into the part of the sleeve 1 that was to form the bottom part of the paper container 10, and the heated air containing the sterilizer was blasted from the small openings 32 for 2 seconds.

In advance, $10^4$, $10^5$ and $10^6$ B. atrophaeus ATCC9372 spores were put on the inner surfaces of the sleeves 1 that were to form the bottom parts of the paper container 10.

After the heated air containing the sterilizer was blasted, the sleeves 1 were molded into the paper containers 10 by the bottom part permanently folding apparatus 7 permanently folding each sleeve 1 along the bottom part forming line 23b, and bonding the folded parts together under pressure with the triangular parts abutting against each other to form the bottom part of the paper container 10, as shown in FIG. 1. Furthermore, the same sterilizer gas as the sterilizer gas used for sterilization of the bottom part was blasted to the inner surfaces of the paper containers 10 for 2 seconds. Furthermore, hot air at 120° C. was blasted to the inner surfaces of the paper containers 10 from the hot air nozzles 17 shown in FIG. 1 at a flowrate of 400 L/min per nozzle for 4 seconds.

After that, the paper containers 10 were filled with 200 ml of SCD bouillon medium and sealed by heat sealing by blasting heated air to the inner surfaces of the top parts of the paper containers 10. The resulting sealed aseptic filled products 11 were kept 35° C. for one week for culture.

Comparative Example

As a comparative example, heated air containing no sterilizer was blasted to the inner surfaces of the sleeves 1 that were to form the bottom parts of the paper containers under the same conditions as in the above example. The subsequent operations were the same as those in the above example.

(Method of Measuring Sterilization Effect)

After the culture, based on the number of paper containers that were positive and the number of paper containers that were negative, the number of living bacteria was calculated by MPN, and the sterilization effect was calculated in units of Log (number of adhering bacteria/MPN).

(Result of Example and Comparative Example)

The sterilization effect in the example was 6.8, whereas the sterilization effect in the comparative examples was 1.6.

In the example described above, the bacteria adhering to the inner surface of the bottom part of the sleeve 1 was able to be killed by blasting the heated air containing hydrogen peroxide to the surface. On the other hand, blasting heated air containing no sterilizer did not provide a sufficient sterilization effect.

The present invention is configured as described above. However, the present invention is not limited to the embodiment described above, and various modifications can be made without departing from the spirit of the present invention.

REFERENCE SIGNS LIST 1 sleeve
5 mandrel having small openings
10 paper container
11 aseptic filled product
15 aseptic filling system
25 sterilizer gas generator
29 blower
30 sterilizing filter
31 heating apparatus
32 small opening
33 mixing apparatus

The invention claimed is:

1. A method for sterilizing a sleeve in an aseptic filling system that molds the sleeve into a paper container having a bottomed tubular shape by closing surfaces of an open end part of the sleeve and performs sterilization, filling and sealing of the paper container, the sleeve being a tubular body having walls formed by laminating at least paper, wherein, in a state where the sleeve stands in a columnar shape, a heated air containing a sterilizer is blasted to inner surfaces of the sleeve, the heated air being set to melt a thermoplastic resin on the inner surfaces of the sleeve, which forms a bottom part of the paper container, to simultaneously sterilize and heat the inner surfaces of the sleeve that forms the bottom part for closing the bottom part, and wherein after heating the inner surfaces of the sleeve that form the bottom part, folding the bottom part of the sleeve along a bottom part forming line and bonding the folded bottom part of the sleeve together under pressure thereby forming the bottom part.

2. The method for sterilizing a sleeve according to claim 1, wherein the heated air containing the sterilizer is blasted by a mandrel that has a small opening and is to be inserted into the sleeve of the columnar shape.

3. The method for sterilizing a sleeve according to claim 2, wherein the sterilizer contains at least hydrogen peroxide.

4. The method for sterilizing a sleeve according to claim 2, wherein the heated air containing the sterilizer is produced by spraying the sterilizer into an evaporation portion to gasify the sterilizer and mixing the gasified sterilizer with heated air.

5. The method for sterilizing a sleeve according to claim 1, wherein the sterilizer contains at least hydrogen peroxide.

6. The method of sterilizing a sleeve according to claim 5, wherein the heated air containing the sterilizer is produced by spraying the sterilizer into an evaporation portion to gasify the sterilizer and mixing the gasified sterilizer with heated air.

7. The method for sterilizing a sleeve according to claim 1, wherein the heated air containing the sterilizer is produced by spraying the sterilizer into an evaporation portion to gasify the sterilizer and mixing the gasified sterilizer with heated air.

* * * * *